(12) United States Patent
Roe

(10) Patent No.: US 6,800,662 B2
(45) Date of Patent: Oct. 5, 2004

(54) METHOD OF REPELLING INSECTS

(75) Inventor: R. Michael Roe, Apex, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 10/176,724

(22) Filed: Jun. 21, 2002

(65) Prior Publication Data

US 2003/0083387 A1 May 1, 2003

Related U.S. Application Data

(63) Continuation-in-part of application No. 09/808,499, filed on Mar. 14, 2001, now Pat. No. 6,437,001.

(51) Int. Cl.[7] ............................................. A01N 35/02
(52) U.S. Cl. ............... 514/675; 514/919; 424/DIG. 10; 504/101; 504/348
(58) Field of Search ............................ 514/675, 919; 424/DIG. 10; 504/101, 348

(56) References Cited

U.S. PATENT DOCUMENTS

| | | | |
|---|---|---|---|
| 2,283,471 A | | 5/1942 | Swaine et al. |
| 4,562,794 A | * | 1/1986 | Speckman ................. 119/651 |
| 5,587,401 A | | 12/1996 | VanderMeer et al. |
| 6,258,857 B1 | * | 7/2001 | Iijima et al. .................... 516/1 |
| 6,437,001 B1 | * | 8/2002 | Roe ........................... 514/675 |

FOREIGN PATENT DOCUMENTS

| | | |
|---|---|---|
| JP | 9-30906 | 2/1997 |
| WO | WO 98/53678 | 12/1998 |
| WO | WO98/53678 | 12/1998 |

OTHER PUBLICATIONS

Chemical abstract 126:208547 (1997).*
Linderman, Russell J., et al., *Inhibition of Insect Juvenile Hormone Esterase by α,β–Unsaturated and α–Acetylenic Trifluoromethyl Ketones, Pesticide Biochemistry and Physiology*, vol. 35, pp. 291–299 (1989).
Rochat, Didier, et al., *Identification of Pheromone Synergists in American Palm Weevil, Rhynchophorus palmarum, and Attraction of Related Dynamis borassi, J. Chem. Ecol*, vol. 26(1), pp. 155–187 (2000).
Renou, M., et al., *Effects of Trifluoromethyl Ketones and Related Compounds on the EAG and Behavioural Responses to Pheromones in Male Moths, Chem. Senses*, vol. 22(4), pp. 407–416 (1997).

Rosell, Gloria, et al., *New Trifluoromethyl Ketones as Potent Inhibitors of Esterases:$^{19}$F NMR Spectroscopy of Transition State Analog Complexes and Structure–Activity Relationships, Biochemical and Biophysical Research Communications*, vol. 226, pp. 287–292 (1996).
Yoshizawa, Takumi et al., *Attractancy of Some Methyl Ketones Isolated from Cheddar Cheese for Cheese Mites, Bochu–Kagaku*, vol. 35(2), pp. 43–45 1970).
Szauman–Szumski, K.J., et al., *Identification of chemicals attractive to the olive bark beetle, Phloeotribus scarabaeoides, in laboratory bioassays*, vol. 43, pp. 345–355 (1998).
*Chemical Abstracts*, 125:208547, Abstracting JP 9–30906 (1997).
*CABA Abstract*, Accession No. 86:48796 (1985).
Du, Y. J., et al., *Electroantennogram and oviposition bioassay responses of Culex quinquefasciatus and Culex tarsalis . . . , Journal of Medical Entomology*, vol. 36, No. 2, pp. 158–166 (1999).
Kramer, K.J, et al., Abstract, *Effects of 2–tridecanone and analogues on the reproduction and mortality of stored product insects, Journal of the Kansas Entomological Society*, vol. 58, No. 2, pp. 254–260.
Sakata, Naohiro, et al., Abstract, *Long–lasting insect repellents containing 2–undecanone and their mats, Chemical Abstracts*, vol. 126, No. 16, pp. 189 (1997).
Du, et al., *Electroantennogram and Oviposition Bioassay Responses of Culex quinquefasciatus and Culex tarsalis (Diptera: Culicidae) to Chemicals in Odors from Bermuda Grass Infusions, Journal of Medical Entomology*, vol. 36, No. 2, pp. 158–166 (1999).
International Search Report for International Application Ser. No. PCT/US02/07620 dated Sep. 26, 2002.

* cited by examiner

*Primary Examiner*—John Pak
(74) *Attorney, Agent, or Firm*—Myers Bigel Sibley & Sajovec

(57) ABSTRACT

A method of repelling an insect pest such as a tick, mosquito or cockroach comprises applying to a subject or substrate, in an amount effect to repel the insect pest, a compound of Formula I:

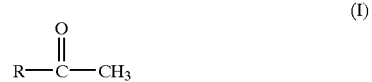

(I)

wherein R is C4–C20 linear or branched alkyl. Particularly preferred compounds of Formula (I) are 2-tridecanone and 2-undecanone.

20 Claims, No Drawings

METHOD OF REPELLING INSECTS

RELATED APPLICATIONS

This application is a continuation-in-part of U.S. patent application Ser. No. 09/808,499 Filed Mar. 14, 2001, which is now U.S. Pat. No. 6,437,001, the disclosure of which is incorporated by reference herein in its entirety.

FIELD OF THE INVENTION

The present invention concerns methods and formulations for repelling insects, particularly for repelling mosquitoes and ticks.

BACKGROUND OF THE INVENTION

Insect repellants are widely used throughout the United States and throughout the world. In some regions, the use of insect repellants is critical to avoiding or reducing the occurrence of disease carried by insects. For example the Centers for Disease Control (CDC) receives nearly 10,1000 reports of Lyme disease (transmitted by deer ticks) and 1,000 reports of encephalitis (transmitted by mosquitoes) annually).

Currently, the most common insect repellent is N,N-diethyl-meta-toluamide (DEET). DEET was designed to be applicable to the skin of subjects, and is designed to repel rather than kill insects. Although in use for some time, concern has recently emerged about the potential toxicity of DEET to children. Recently the US Environmental Protection Agency (EPA) determined that it would no longer allow child safety claims on labels for DEET-containing products.

The United States EPA Facts: Methyl Nonyl Ketone (July 1995) describes methyl nonyl ketone as a dog and cat repellent/training aid and iris borer deterrent, but does not suggest its use as an insect repellent.

U.S. Pat. No. 2,283,471 to Swaine describes the use of compounds such as methyl nonyl ketone and methyl undecyl ketone as contact insecticides for aphids and similar piercing-sucking insects (all primitive plant-feeding insects) which require contact insecticides for their control, but does not suggest their use as insect repellents.

R. Linderman et al., *Pesticide Biochemistry and Physiology* 35, 291–299 (1989), describes the inhibition of insect juvenile hormone esterase by α,β-unsaturated and α-acetylenic trifluoromethyl ketones, but does not suggest the use thereof as insect repellents.

Accordingly, there remains a need for new ways to repel insects, particularly mosquitoes and ticks.

SUMMARY OF THE INVENTION

Accordingly, the present invention provides a method of repelling an insect pest, comprising applying to a subject or substrate, in an amount effect to repel the insect pest, a compound of Formula I:

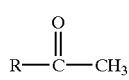
(I)

wherein R is C4–C20 linear or branched alkyl, preferably linear and preferably C7 to C13 alkyl.

Particularly preferred insects for application of the present method are mosquitoes, ticks and cockroaches.

In one preferred embodiment, the insect for application of the present method is a thrip.

In another embodiment, the insect for application of the present method is a biting fly such as a deer fly.

In another embodiment, the insect for application of the method of the present invention is a gnat.

In another embodiment, the insect for application of the method of the present invention is an aphid.

Further aspects of the present invention include compositions comprising compounds of Formula (I), or other active compounds, in combination with carriers or other ingredients for repelling insects, and the use of compounds of Formula (I) or active compounds disclosed herein for the preparation of a composition for repelling insects.

DETAILED DESCRIPTION OF THE PREFERRED EMBODIMENTS

As used herein, the term "alkyl" (e.g., alkyl, alkylcarboxy, alkylphenyl,etc.) refers to a straight or branched chain hydrocarbon having from 4 to 20 carbon atoms, which alkyl may be linear or branched. The alkyl may optionally be substituted with substituents selected from the group which includes halo, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by a substituent selected from the group including alkyl, nitro, cyano, halo and lower perfluoroalkyl, multiple degrees of substitution being allowed. Examples of "alkyl" as used herein include, but are not limited to, n-butyl, n-pentyl, isobutyl, pentyl, hexyl, octyl, nonyl, undecyl, the like.

The term "loweralkoxy" as used herein means linear or branched $C_1$ to $C_4$ alkoxy, preferably methoxy, ethoxy, or propoxy.

The term "halo" as used herein means halogen, preferably fluoro, chloro, bromo or iodo, most preferably fluoro.

Subjects to be treated with compounds of the present invention include both human and animal subjects (e.g., dogs, cats, horses, cattle). Subjects may be directly or indirectly treated, such as by applying the active compound to the skin of the subject, or by applying the active compound to an article worn by or otherwise protecting the subject.

Substrates to be treated with compounds of the present invention include, but are not limited to, floors, plants, containers, walls, pools or open bodies of water, etc.

Insects that may be repelled by the methods of the present invention include ticks, fleas, cockroaches, and biting flies, typically of the order diptera, and further including mosquitoes, horse flies, deer flies, black flies, gnats, no-see ums, chiggers, etc.

The term "mosquito" as used herein concerns any type of mosquito (e.g., Anopheles, Aedes, and Culex), including but not limited to Tiger mosquitoes, *Aedes aboriginis, Aedes Aegypti, Aedes, albopictus, Aedes cantator, Aedes sierrensis, Aedes sollicitans, Aedes squamiger, Aedes sticticus, Aedes vexans, Anopheles quadrimaculatus, Culex pipiens*, and *Culex quinquefaxciatus*.

The term "tick" as used herein includes any type of tick, including but not limited to, deer ticks, the American dog tick (*Dermacentor variabilis*), *Ornithodoros parkeri, O. moubata,* and *Dermacentor andersoni*.

The term "cockroach" as used herein refers to any type of cockroach, including but not limited to the American cockroach (*Periplaneta americana*), German cockroach (*Blattella germanica*), oriental cockroach (*Blatta orientalis*), wood cockroach (*Parcoblatta pennsylvanica*), brownbanded cockroach (*Supella longipalpa*), and smokybrown cockroach (*Periplaneta fuliginosa*).

Other insect that can be treated by the methods of the present invention include, but are not limited to: thrips, biting flies such as deer flies, gnats, aphids, lice (Order Phthiraptera), such as head and body lice of humans, *Pediculus humanus capitis* and *P. H. humanus*; Fleas (Order Siphonaptera), such as cat and dog fleas, Ctenocephalides sp. human fleas, Echidnophaga, Pulex sp. Bees, wasps and ants (Order Hymenoptera) mites such as *Sarcoptes scabei* (human itch mite) the North American chigger or red bug, Trombicula sp. nematodes such as human parasitic nematodes, Silverfish (Order Thysanura), such as *Lepisma saccharina*, firebrat, *Thermobia domestica;* Termites (Order Isoptera) such as *Reticulitermes flavipes, Incisitermes minor, Marginitermes hubbardi,* and *Cryptotermes brevis*; Earwigs (Order Dermaptera); Psocids (Order Psocoptera) such as booklice; Beetles (Order Coleoptera), particularly wood eating beetles; Centipedes such as Lithobius, Geophilus, Scutigera and millipides such as *Julus terrestris;* Scorpions such as *Centruroides sculpturatus* and *Mastigoproctus gianteus;* etc.

1. Repellant Compounds

Active compounds or compounds of Formula I herein are either known and may be produced in accordance with techniques known to those skilled in the art, or where novel may be produced by variations of known techniques which will be apparent to those skilled in the art.

2-tridecanone (methyl undecyl ketone) is commercially available from the Sigma-Aldrich Company, P.O. Box 2060, Milwaukee, Wis. 53201 USA as catalog number 17,283-9.

2-undecanone (methyl nonyl ketone) is commercially available from the Sigma-Aldrich Company, P.O. Box 2060, Milwaukee, Wis. 53201 USA as catalog number U-130-3.

2. Methods and Formulations for Repelling Insects

The present invention provides repellant compounds, compositions comprising said repellant compounds and the use of such repellant compounds and compositions in controlling pests, particularly insect pests such as mosquitoes.

Liquid formulations may be aqueous-based or non-aqueous (i.e., organic solvents), or combinations thereof, and may be employed as foams, gels, suspensions, emulsions, microemulsions or emulsifiable concentrates or the like. The ingredients may include rheological agents, surfactants, emulsifiers, dispersants or polymers.

In one embodiment, a floor wax composition may include repellant compounds as described herein, in an amount effective to repel cockroaches that might otherwise feed upon the composition once applied to floors, or to simply repel cockroaches from floor surfaces to which they are applied.

As will be appreciated by a person skilled in the art, the repellant concentration will vary widely depending upon the nature of the particular formulation, particularly whether it is a concentrate or to be used directly. The repellant compound will be present in the composition in a concentration of at least about 0.0001% by weight and may be 10, 50, 99 or 100% by weight of the total composition. The repellant carrier may be from 0.1% to 99.9999% by weight of the total composition. The dry formulations will have from about 0.0001–95% by weight of the pesticide while the liquid formulations will generally have from about 0.0001–60% by weight of the solids in the liquid phase.

The formulations may be applied to the subject's skin, or may be applied to garments, belts, collars, or other articles worn by the subject from whom insects are to be repelled.

The formulation may be applied to netting or screening that protects a subject, particularly a sleeping subject. The formulations may be applied to non-animal substrates from which insects are to be repelled, such as plants. Application to subjects or substrates may be carried out by spraying, dusting, sprinkling or the like.

The compounds according to the present invention may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, etc., if desired, in the form of particular dosage preparations for specific application made therefrom, such as solutions, emulsions, suspensions, powders, pastes, and granules as described herein or as otherwise known in the art which are thus ready for use.

The repellant compounds may be administered with other insect control chemicals, for example, the compositions of the invention may employ various chemicals that affect insect behavior, such as insecticides, attractants and/or repellents, or as otherwise known in the art. The repellant compounds may also be administered with chemosterilants.

The repellant compounds are suitably applied by any method known in the art including, for example, spraying, pouring, dipping, in the form of concentrated liquids, solutions, suspensions, sprays, powders, pellets, briquettes, bricks and the like, formulated to deliver a repellant effective concentration of the repellant compound. The repellant formulations may be applied in a repellant effective amount to an area of pest infestation or an area susceptible to infestation, a body of water or container, a barn, a carpet, pet bedding, an animal, clothing, skin, and the like.

The following examples are illustrative of the practice of the present invention, and should not be construed as limiting thereof. All percentages are by weight and all solvent mixture proportions are by volume unless otherwise noted.

EXAMPLE 1

Mosquito Repellant

Untreated cheese cloth was wrapped around the right hand of a human subject and inserted into a cage of adult tiger mosquitoes (approximately 50 in the cage). The insects were immediately attracted to the subject's hand. The tiger mosquitoes were observed to be actively probing and biting the subject's hand through the cheese cloth within seconds. The subject was required to shake his hand violently to remove the insects from the cheese cloth when removing his hand from the cage, to avoid transferring the insects from the cage to the outside.

The same cheese cloth was then treated to saturation with a 1% by volume solution of 2-tridecanone/2-undecanone (approximately 50% by volume of each) in ethanol. The cloth was allowed to air dry to remove the ethanol.

After treatment as described above the cheese cloth was again wrapped around the subject's hand and placed in the same cage. Fewer (by 1/10) mosquitoes landed on the cheese cloth. This treatment was performed within five minutes of the control experiment described above. When mosquitoes did land on the cheese cloth, they were observed to remain thereon for only approximately 1 to 2 seconds and then fly off. No probing was observed, no bites were received, and the subject was able to easily remove his hand from the cage without risk of transferring mosquitoes.

EXAMPLE 2

Tick Repellency of 2-undecanone

A volume of 800 microliters of a 1% by volume solution of 2-undecanone and 2-tridecanone mix (50% each) in ethanol was added to one-half of a coarse 9 centimeter filter paper disc placed in a plastic petri plate of corresponding size and allowed to air dry. An exact control half filter paper disc was treated in a separate container with 800 microliters of ethanol at the same time. The control was allowed to air dry until no ethanol could be detected by smell approximately 2 centimeters from the surface of the filter paper. The treatment and ethanol control was then transferred to a sterile plastic petri plate containing 10 ticks, Ornithodorus parkeri. The control and treatment paper were positioned so that they covered most of the bottom of the plate but did not touch in the middle; they were separated by a distance of about 0.25 cm. The ticks were randomly distributed around the plate when the filter paper was introduced. Essentially 100% of the ticks were found on the ethanol control for 5 minutes through 3 hours. At three observation periods, 14 minutes, 1 hour and 2 hours, one tick was found at the margin between the two treatments. The experiment was run at room temperature and in the dark. Observations were made in normal laboratory light and took only a few seconds.

EXAMPLE 3

Mosquito Repellency of 2-undecanone

Forty milliliters of a 2.5 percent solution of 2-undecanone in absolute ethanol was added to a gauze glove (20×15 centimeters) in a 250 milliliter beaker. After soaking for 1 minute, the glove was laid onto aluminum foil in a fume hood for 13 minutes and then suspended by one end from the sash of the fume hood for 3 minutes. The ethanol appeared to be completely evaporated after this treatment as determined by touch. Upon touch, the glove did not feel wet or cool. The same treatment was used without 2-undecanone as a control. After the same drying steps, no odor of ethanol could be detected by smell. The control glove was the same physical dimensions and made from the same batch of material as the treatment. The control experiments including wetting and drying of the glove was conducted prior to the 2-undecanone treatment.

Approximately 100 adult male and female mosquitoes (Aedes taeniorhynchus) (exact sex ratio not determined) were placed in a 12×12×14.5 inch stainless steel screened cage. The cage was fitted with a cloth stocking on one side to allow material to be added and removed from the cage by hand without allowing the mosquitoes to escape. The mosquitoes were added to the cage approximately 12 hours before the test. Two 1 ounce plastic cups containing 2–3 KIM WIPES™ brand paper wipes wetted with 20% sucrose in water were placed into the cage for a source of food and water. The insects were held over night for acclimation at 27 degrees Centigrade, 14:10 LD cycle and 50% relative humidity. The next morning, a few mosquitoes were seen resting on the sucrose feeding stations.

The following data are the control responses when the tester's hand covered by the ethanol treated (dried) glove was placed into the mosquito cage (at room temperature) for 20 seconds at the times indicated: 0 minutes, 10 landings and 1 bite; 10 minutes, 9–12 landings and 1 bite; 20 minutes, approximately 13 landings and no bites; and 40 minutes, approximately 13 landings and no bites. As soon as the tester's hand entered the cage, the mosquitoes demonstrated obvious host seeking behavior which including flying around the cage and in the near region of the tester's hand. However, only sustained landings of about 5 seconds were recorded as a positive response along with actual bites. After the conclusion of the control experiments, the tester's hand covered by the 2-undecanone treated (dried) glove was placed into the mosquito cage (at room temperature) for 20 seconds at the times indicated: 0 minutes, 15 minutes, 25 minutes, 50 minutes, 1 hour and 40 minutes, 2 hours and 40 minutes, 3 hours and 40 minutes, and 4 hours and 40 minutes. No landings and no bites were noted at any of these time points. During the first 3 to 4 hours, the mosquitoes demonstrated no host seeking behavior, such as even trying to fly toward the tester's hand.

In conclusion, under the treatment conditions described above, 2-undecanone was effective as a mosquito repellent for greater than 4 hours and 40 minutes.

EXAMPLE 4

Cockroach Repellency of 2-undecanone

1. Dispersion of 2-undecanone in Floor Wax. A commercially available paste floor wax is combined with one percent by weight of 2-undecanone and the two ingredients mixed thoroughly together. The paste floor wax is then applied to a region of flooring and buffed. The same paste floor wax, without 2-undecanone, is applied to an adjacent region of flooring in the same amount and also buffed. When released onto each region of flooring, cockroaches are found to spend less time in the region containing 2-undecanone than in the control region that does not contain 2-undecanone.

2. Dispersion of Solutions of 2-undecanone in Ethanol. The repellency of 2-undecanone to the German cockroach (Blattella germanica L.) was further examined using the following protocol. Semicircular test papers (4.5 cm radius) of FISHER brand filter paper were saturated with 240 microliters of 13.25 micrograms/microliter 2-undecanone in 100% ethanol or 100% ethanol alone as a negative control. The filter papers were placed on an aluminum foil sheet, and allowed to dry for one hour in a fume hood. The described semicircular-test papers were then placed in glass sterile petri dishes (internal diameter 9 cm), two papers in one dish, one containing 2-undecanone and the other containing ethanol only. The filter paper semicircles were arranged as to completely fill the bottom of the petri dish. All the other internal surfaces of the petri dishes were greased with pure Vaseline to prevent cockroaches from crawling to these areas. German cockroaches (10 two week old male adults, or two day old females) were randomly transferred to the surface of the test papers in the above described petri dish. The petri dish was covered with a dish top, the covered plate placed into a plastic container (3⅛ cups/25 oz/739 ml Glad Ware® Entrée containers with a paper towel at the bottom containing 5–6 ml of distilled water), the container was tightly sealed with the matching lid, and the Glad container containing the tests placed into a dark room at room temperature. The location of cockroaches was recorded at 1, 2, 4, 8, 24 and 48 hours. The results of these experiments are outlined in Table 1. These results show that German cockroaches spend less time on 2-undecanone treated (Un) test papers compared to the ethanol (Et) negative control.

TABLE 1

2-Undecanone Repellent Test for German Cockroach
Number of insects on test papers (total = 10 in each treatment)

|  | 1 h | | 2 h | | 4 h | | 8 h | | 24 h | | 48 h | |
|---|---|---|---|---|---|---|---|---|---|---|---|---|
| Treatment | Et | Un | Et | Un | Et | Un | Et | Un | Et | Un | Et | Un |
| Male 1 | 9 | 1 | 9 | 1 | 10 | 0 | 10 | 0 | 10 | 0 | 7 | 3 |
| Male 2 | 9.5 | 0.5 | 10 | 0 | 10 | 0 | 10 | 0 | 10 | 0 | 6 | 4 |
| Male 3 | 9 | 1 | 10 | 0 | 10 | 0 | 10 | 0 | 10 | 0 | 10 | 0 |
| Female 1 | 9 | 1 | 10 | 0 | 10 | 0 | 10 | 0 | 8 | 2 | 5 | 5 |
| Female 2 | 9 | 1 | 9 | 1 | 10 | 0 | 9 | 1 | 10 | 0 | 6 | 4 |
| Female 3 | 8 | 2 | 9 | 1 | 9.5 | 0.5 | 10 | 0 | 7 | 3 | 4 | 6 |

EXAMPLE 5

Undecanone Repellency of Western Flower Thrips
(*Frankliniella occidentalis*)

Bean tails were cut into 5–6 cm length with a sharp razor blade, and glued cut side down into 5 cm glass petri dishes with carpenter's glue, two per dish, 2–3 cm apart. The dishes were then placed into plastic containers (bottom diameter 8 cm, top diameter 11 cm, height 8 cm), the lid closed, and incubated at room temperature overnight. Each glued bean tail was then coated with either 80 $\mu$l 2-undecanone solution (13.35 $\mu$g/$\mu$l in 100% ethanol) or 100% ethanol (negative control), then air dried for one hour in a fume hood at room temperature. Five larval thrips were then transferred onto each glued bean using a camelhair brush. The lid of the container was sealed and the insects incubated at room temperature on a lab bench. The location of thrips were recorded at 1, 2, 4, 8, 24 and 48 hours. The results of this study are listed in Table 2. These results indicate that a lower number of thrips spend time on the 2-undecanone treated bean tails (Un) as compared to the ethanol (Et) negative control.

TABLE 2

2-Undecanone Repellent Rest for Western Flower Thrips
Number of insects on beans (total insects = 10 per treatment)

|  | 1 h | | 2 h | | 4 h | | 8 h | | 24 h | | 48 h | |
|---|---|---|---|---|---|---|---|---|---|---|---|---|
| Treatment | Et | Un | Et | Un | Et | Un | Et | Un | Et | Un | Et | Un |
| 1 | 6 | 3 | 8 | 1 | 8 | 1 | 8 | 0 | 9 | 1 | 8 | 0 |
| 2 | 5 | 5 | 5 | 4 | 6 | 3 | 7 | 1 | 7 | 2 | 7 | 1 |
| 3 | 7 | 1 | 6 | 2 | 7 | 1 | 8 | 2 | 8 | 0 | 8 | 1 |
| 4 | 5 | 5 | 5 | 4 | 5 | 3 | 6 | 1 | 6 | 2 | 7 | 3 |
| 5 | 4 | 2 | 7 | 1 | 9 | 0 | 8 | 0 | 9 | 1 | 9 | 0 |
| 6 | 5 | 5 | 4 | 4 | 7 | 2 | 8 | 2 | 7 | 2 | 5 | 1 |

EXAMPLE 6

Deer Fly and Gnat Repellency of 2-undecanone

The research described was conducted in Middlesex, N.C. at midday in late spring. A single lane gravel road 0.5 miles in length through a pine/hard wood mixed forest was divided into five 0.1 mile segments. The human subject walked all five segments at the rate of 2 min and 45 seconds per 0.1 mile in one direction for the control and in the reverse direction for the 2-undecanone treatment. Insect landings on the subject's head were counted by two observers that walked along side (on the left and on the right of) the human subject at a distance of about two feet. A landing was defined as the insect standing on the surface of the head (on the hair or face) for at least 1–2 seconds. After a landing was recorded, the observer waived their hand toward the deer fly causing the insect to take flight. Gnat density flying around the head was scored as high (greater than 100 gnats), moderate (about 50), or low (less than 20). The frequency of gnats landing on the human subject was not recorded because of their small size and their rapid movements on and off the subject's head. At the end of each 0.1 mile segment of the walk, the number of deerfly landings were recorded as well as the average density of gnats noted. At the end of the control walk, the head (hair and face) of the human subject was treated with a solution of 20% 2-undecanone in isopropyl alcohol by 5 spray pumps from the standard sprayer. Three minutes after spraying, the human subject reversed the 0.5 mile walk. The results of this study are depicted in Table 3. The number of deer fly landings after 2-undecanone treatment was 64% of that observed for the untreated control. For Gnats, the density was reduced after 2-undecanone treatment from high (>100) to low (<20).

TABLE 3

Effect of 2-Undecanone on Deer Fly Landings and Gnat Density

|  | Deer Fly Landings | | Gnat Density | |
|---|---|---|---|---|
| Segment (0.1 Mi) | Control | Treatment | Control | Treatment |
| 1 | 1 | 0 | High | High |
| 2 | 0 | 0 | High | Low |
| 3 | 4 | 3 | High | Low |
| 4 | 7 | 3 | High | Low |
| 5 | 16 | 4 | High | Low |
| TOTAL | 28 | 10 | High | Low |

EXAMPLE 7

Aphid Repellency of 2-undecanone

Green peach aphids on tobacco leaves in the greenhouse were removed from the whole plant by cutting the leaf from the main stalk and then the detached leaves containing aphid immediately transported to the Roe lab. A 17 mm diameter leaf disc was prepared with an appropriately sized cork borer and the leaf disc containing aphids placed in the center of a plastic container (bottom diameter 90 mm, top diameter 115 mm, height 44 mm). The bottom was lined with two moistened filter papers and leaf disc(s) placed onto the wetted filter paper. Control and treated leaf discs without aphids were placed adjacent to the plant disc containing aphids, and the container closed with a plastic lid. After a period of time, the aphids were counted. The results of these experiments are shown in Table 4.

TABLE 4

Number of aphids vs.
time that moved to the plant disc(s) with no aphids

| Treatments and replications | Aphids on the aphid disc | Number of insects that moved to the treated disc | | | |
|---|---|---|---|---|---|
| | | 2 h | 4 h | 19 h | 24 h |
| C | 70 | 3 | 5 | 15 | 13 |
| C | 86 | 5 | 6 | | 21 |
| C | 64 | 3 | 4 | | 17 |
| A | 90 | 1 | 3 | 16 | 12 |

TABLE 4-continued

Number of aphids vs.
time that moved to the plant disc(s) with no aphids

| Treatments and replications | Aphids on the aphid disc | Number of insects that moved to the treated disc | | | |
|---|---|---|---|---|---|
| | | 2 h | 4 h | 19 h | 24 h |
| A | 70 | 3 | 6 | | 19 |
| A | 80 | 3 | 3 | | 20 |
| B | 50 | 0 | 0 | 0 | 0 |
| B | 45 | 0 | 0 | | 0 |
| B | 61 | 0 | 0 | | 0 |
| D-C | | 2 | 3 | 8 | 7 |
| --A | 100 | 0 | 2 | 3 | 5 |
| --B | | 0 | 0 | 0 | 0 |
| D-C | | 2 | 3 | | 12 |
| --A | 90 | 1 | 4 | | 11 |
| --B | | 0 | 0 | | 0 |
| D-C | | 3 | 5 | | 9 |
| --A | 85 | 4 | 4 | | 7 |
| --B | | 0 | 0 | | 0 |

The treatments noted in Table 4 are further detailed below

Treatment A: The leaf disc without aphids was sprayed with ethanol alone (solvent control). After spraying, the disc was placed into a fume hood and the solvent allowed to evaporate for 40 min before it was added to the test chamber.

Treatment B: The leaf disc without aphids was sprayed with 20 percent 2-undecanone in ethanol (v/v) and the solvent allowed to evaporate for 40 minutes in a fume hood before it was added to the test chamber.

Treatment C: Leaf disc without aphids and without spray (just an untreated fresh leaf).

Treatment D: Placed discs without aphids treated according to A, B and C adjacent to aphid disc.

The results shown in Table 4 indicate that aphids do not move from the aphid disk to disks treated with 2-undecanone, and indicates that 2-undecanone is effective at repelling aphids over the 24 hour test period.

The foregoing is illustrative of the present invention, and is not to be construed as limiting thereof. The invention is defined by the following claims, with equivalents of the claims to be included therein.

That which is claimed is:

1. A method of repelling mosquitoes comprising applying to a subject an effective amount of a repellant comprising 2-undecanone, wherein said mosquitoes comprise at least one mosquito species selected from the group consisting of Tiger mosquitoes, *Aedes aboriginis, Aedes Aegypti, Aedes albopictus, Aedes cantator, Aedes sierrensis, Aedes sollicitans. Aedes squamiger, Aedes sticticus, Aedes vexans, Anopheles quadrimaculatus, Culex pipiens,* and *Culex quinquefaxciatus* and wherein said subject is a mammalian subject.

2. The method of claim 1, wherein said mosquitoes comprise at least one mosquito species selected from the group consisting of *Aedes aboriginis, Aedes Aegypti, Aedes albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefaxciatus.*

3. The method of claim 1, wherein said mosquitoes comprise *Anopheles quadrimaculatus* mosquitoes.

4. The method of claim 1, wherein said mosquitoes comprise at least one mosquito species selected from the group consisting of *Aedes aboriginis, Aedes Aegypti, Aedes albopictus, Aedes canator, Aedes sierrensis, Aedes sollicitans, Aedes squamiger, Aedes sticticus, Aedes vexans* mosquitoes.

5. The method of claim 1, wherein said mosquitoes comprise at least one mosquito species selected from the group consisting of *Culex pipiens* and *Culex quinquefaxciatus* mosquitoes.

6. The method of claim 1, wherein said mammalian subject is a human subject.

7. The method of claim 6, wherein said applying step comprises applying said repellant to the skin of said human subject.

8. The method of claim 6, wherein said applying step comprises application of said repellant to an article, which article is worn by said human subject.

9. The method of claim 6, wherein said repellant further comprises a carrier.

10. The method of claim 9, wherein said repellant further comprises at least one additional agent selected from the group consisting of insecticides, acaricides, rodenticides, fungicides, bactericides, nematocides, herbicides, fertilizers and growth-regulating agents.

11. The method of claim 9, wherein the carrier comprises ethanol.

12. The method of claim 9, wherein the concentration of 2-undecanone in said repellant is from about 0.001% by weight to 10% by weight of the repellant.

13. The method of claim 9, wherein said repellant comprises a liquid formulation containing from about 0.001% to 60% by weight of 2-undecanone.

14. The method of claim 1, wherein said repellant further comprises at least one additional component that affects behavior of said mosquitoes.

15. The method of claim 14, wherein said at least one additional component comprises an additional repellant component.

16. A method of repelling mosquitoes from a locus susceptible to the presence of mosquitoes, comprising applying to said locus an effective amount of a repellant comprising 2-undecanone, wherein said mosquitoes comprise at least one mosquito species selected from the group consisting of Tiger mosquitoes, *Aedes aboriginis, Aedes Aegypti, Aedes albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefaxciatus.*

17. The method of claim 16, wherein said locus is adapted for use or presence of humans and/or animals.

18. The method of claim 17, wherein said locus comprises an article worn by or arranged to protect humans and/or animals.

19. The method of claim 17, wherein said locus comprises a dwelling structure.

20. The method of claim 17, wherein said locus comprises a body of water.

* * * * *